(12) United States Patent
Alali

(10) Patent No.: US 9,050,160 B1
(45) Date of Patent: Jun. 9, 2015

(54) DENTAL FLOSSING DEVICE

(71) Applicant: Ahmad Mohammad Hussain Alali, Bayan (KW)

(72) Inventor: Ahmad Mohammad Hussain Alali, Bayan (KW)

( * ) Notice: Subject to any disclaimer, the term of this patent is extended or adjusted under 35 U.S.C. 154(b) by 0 days.

(21) Appl. No.: 14/526,471

(22) Filed: Oct. 28, 2014

(51) Int. Cl.
*A61C 15/00* (2006.01)
*A61C 15/04* (2006.01)

(52) U.S. Cl.
CPC ............ *A61C 15/048* (2013.01); *A61C 15/046* (2013.01)

(58) Field of Classification Search
CPC .... A61C 15/04; A61C 15/046; A61C 15/048; A61C 15/043; A61C 15/00; A61C 15/047; A61D 15/02
USPC .................. 132/321–329, 309; 433/118, 141; 15/185, 186, 106, 110
See application file for complete search history.

(56) References Cited

U.S. PATENT DOCUMENTS

| | | | |
|---|---|---|---|
| 3,892,249 A | 7/1975 | Jones et al. | |
| 3,927,686 A | 12/1975 | Zambito | |
| 4,051,857 A * | 10/1977 | Zambito | 132/323 |
| 4,253,477 A * | 3/1981 | Eichman | 132/323 |
| 4,920,992 A * | 5/1990 | Preciutti | 132/323 |
| 5,261,430 A | 11/1993 | Mochel | |
| 7,055,531 B2 * | 6/2006 | Rehkemper | 132/322 |
| 7,171,971 B2 | 2/2007 | Ochs et al. | |
| 7,392,810 B2 * | 7/2008 | Apotheker et al. | 132/322 |
| 7,487,785 B2 | 2/2009 | Dougan et al. | |
| D684,724 S | 6/2013 | Tokui et al. | |
| 2001/0054211 A1* | 12/2001 | Cabedo-Deslierres et al. | 15/106 |
| 2007/0261185 A1* | 11/2007 | Guney et al. | 15/22.1 |
| 2009/0165814 A1 | 7/2009 | Welt et al. | |
| 2010/0116287 A1* | 5/2010 | Cohen | 132/323 |
| 2012/0167913 A1 | 7/2012 | Caldwell | |

\* cited by examiner

*Primary Examiner* — Vanitha Elgart
(74) *Attorney, Agent, or Firm* — Richard C Litman

(57) ABSTRACT

The dental flossing device has an elongate handle with a removable and disposable floss holder at its distal end. A slide is installed along the handle, with the slide reciprocating axially along the handle when manipulated by a user of the device. The slide operates a flexible cable that in turn reciprocates the floss holder orthogonally relative to the elongate axis of the handle. Upper and lower bite pads are installed upon the distal end of the handle, with the user of the device gripping the pads, and thus the distal end of the device, between the teeth. The floss extending across the floss holder is then reciprocated between adjacent teeth by operating the slide on the handle. The device can also include a timer and alarm to notify the user of the appropriate time to be spent flossing, and to remind the user to floss daily.

19 Claims, 6 Drawing Sheets

DENTAL FLOSSING DEVICE

BACKGROUND OF THE INVENTION

1. Field of the Invention

The present invention relates generally to dental hygiene, and particularly to a dental flossing device having a reciprocating, disposable floss holder.

2. Description of the Related Art

Nearly all people are well aware of the need for regular tooth brushing in order to remove food deposits that can lead to bacterial buildup and resulting dental problems, e.g., caries (cavities), gingivitis, periodontitis, etc. However, brushing the teeth is not likely to remove all, or nearly all, of the residual food deposits and plaque that can accumulate in the mouth, particularly between the teeth. Accordingly, nearly all dentists and oral hygiene specialists also recommend regular flossing between the teeth in order to remove deposits that typically cannot be removed by brushing.

While most people probably recognize the value of regular flossing, the actual act of flossing between the teeth is often relatively more difficult than brushing. This can be particularly true of individuals with closely spaced teeth, where it can be difficult to work a strand of dental floss between the teeth. Even in the case of individuals having normally spaced teeth, it can likewise be difficult for many individuals to manipulate dental floss, particularly if they are arthritic or have some other infirmity that affects their dexterity.

In addition to the above considerations, many people who floss regularly may do so incorrectly. Proper flossing technique typically requires the floss to be drawn down between the teeth, and then lifted back up between the teeth while being drawn upward along the surfaces of the teeth. Use of an improper technique of drawing the floss back and forth laterally across the bases of the teeth has been known to actually cut grooves across the bases of the teeth after prolonged and continuous use of this procedure, thus doing much more harm than good.

Thus, a dental flossing device addressing the aforementioned problems is desired.

SUMMARY OF THE INVENTION

Embodiments of a dental flossing device include an elongate handle having a handgrip portion and an opposite distal end portion. The distal end portion is adapted for the removable installation of a disposable floss holder thereon. A slide is installed atop the handle, the slide adapted to reciprocate longitudinally in the handle, such as by manipulation by a user of the device. The slide operates a flexible elongate member, such as a flexible cable or the like, with the flexible elongate member, such as the flexible cable, having a distal end within the distal end portion of the handle.

Movement of the flexible elongate member within the handle by operation of the slide results in movement of the distal end of the flexible elongate member, such as in a direction substantially orthogonal to the handle. By movement of the flexible elongate member, the distal end of the flexible elongate member in turn reciprocates the floss holder including dental floss in a substantially orthogonal direction relative to a direction of the main body of the handle. A return spring is provided in communication with the slide to automatically return the slide to an initial position after a longitudinal movement of the slide, such as at the end of each stroke. The length of the stroke of the slide, and therefore the stroke length of the floss holder, can be adjusted by moving the slide to a corresponding position within its channel in the handle.

Embodiments of a dental flossing device include opposed upper and lower bite pads provided on the distal end portion of the handle, the upper bite pad being generally positioned opposite the floss holder and a lower bite pad being generally positioned adjacent to the floss holder. The upper bite pad and the lower bite pad are adapted to respectively engage with teeth of a user of the device. The opposed bite pads are adapted to engage a user's teeth so as to position the distal end of the device between the user's teeth. The slide is then manipulated to move the dental floss and the floss holder downward between two adjacent teeth, with the return spring retracting the dental floss at least partially back up between the teeth via the flexible elongate member, such as a flexible cable.

The floss holder including the dental floss is desirably removably installed upon the distal end of the handle, and is adapted to be disposable for single use operation. A portion of the upper bite pad is desirably selectively removable, as well, to provide a selectively removable retainer for the floss holder.

Embodiments of a dental flossing device can further include a timer and alarm to indicate to the user a proper flossing time span. The alarm can also be actuated, such as once per day, to remind the user to use the dental flossing device.

These and other features of the present invention will become readily apparent upon further review of the following specification and drawings.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
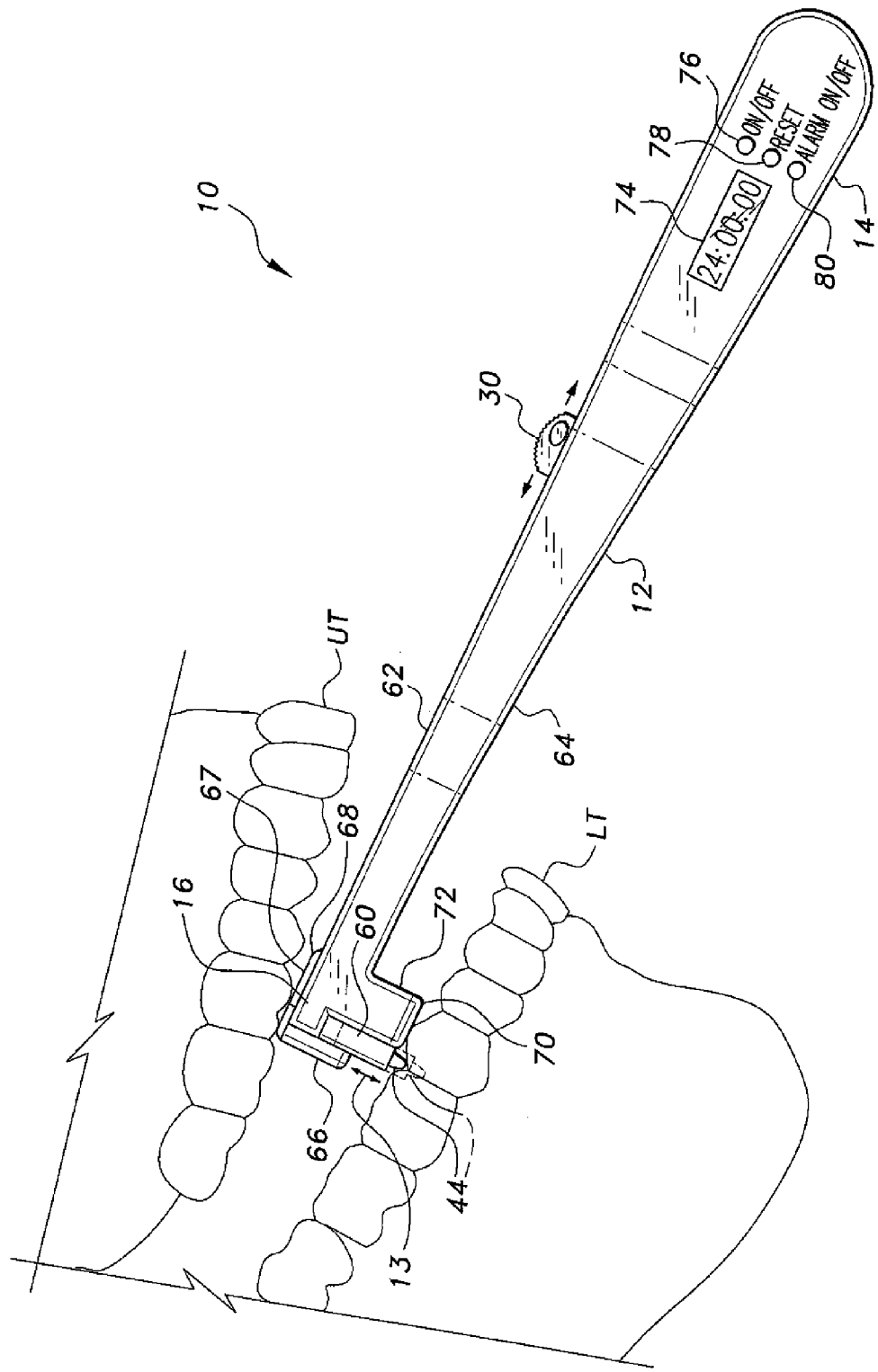
FIG. 1 is an environmental, side elevation view of an embodiment of a dental flossing device according to the present invention, showing its exemplary use and operation.
Figure 2:
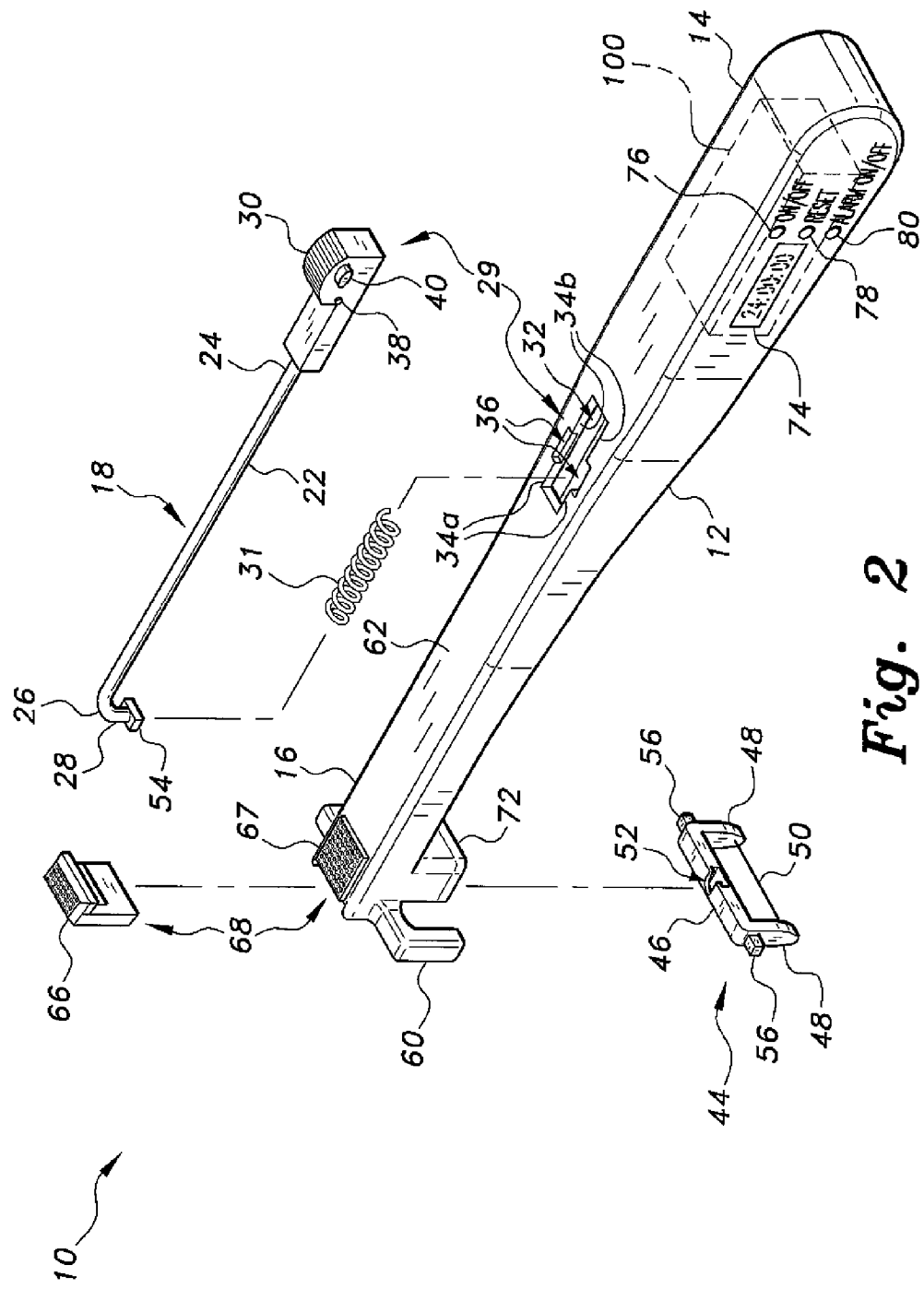
FIG. 2 is an exploded top perspective view of an embodiment of the dental flossing device of FIG. 1 according to the present invention, showing various components thereof and their relationships.
Figure 3:
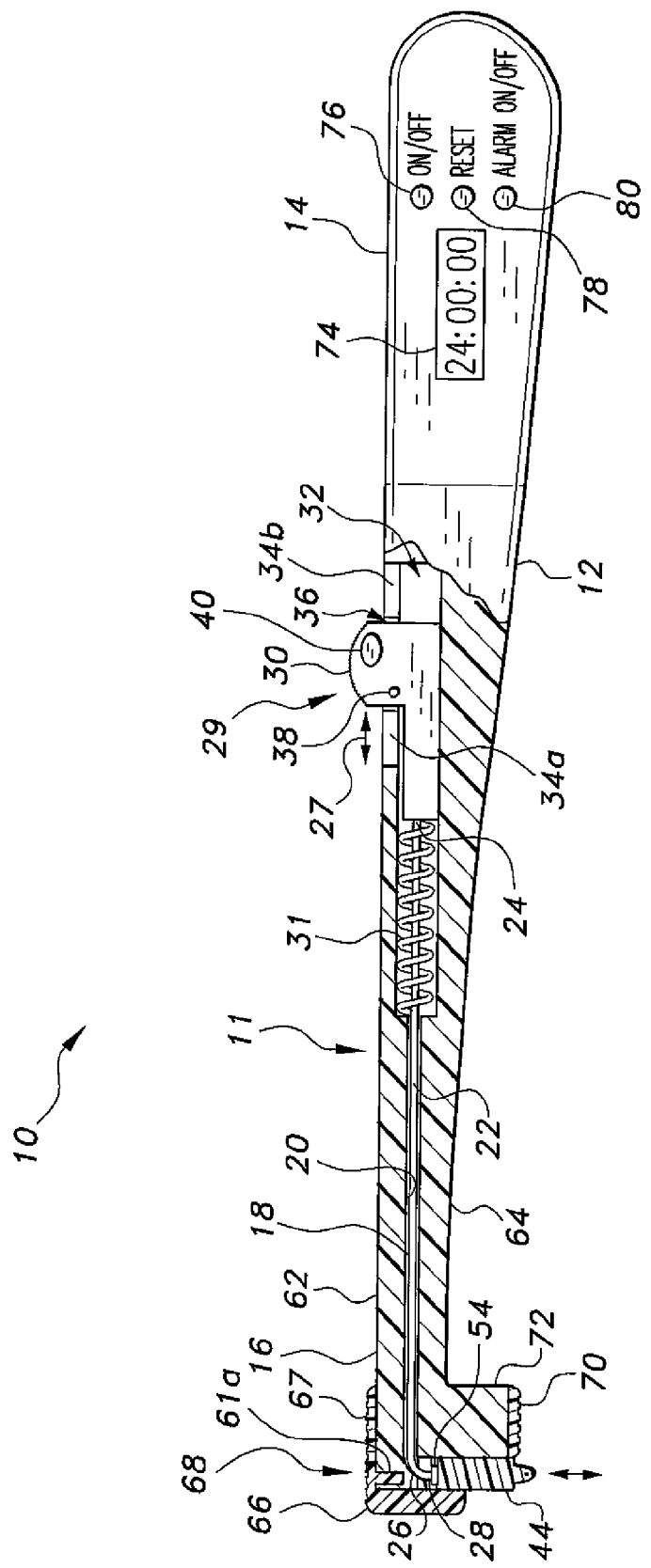
FIG. 3 is a side elevation view in partial section of an embodiment of the dental flossing device of FIG. 1 according to the present invention, showing the internal placement of various components thereof.

Embodiments of a dental flossing device greatly facilitate the act of flossing a user's teeth, due to the reciprocating action of the floss holder and its dental floss as controlled by a manually actuated reciprocating slide on the handle of the dental flossing device. FIG. 1 provides an environmental side elevation view showing an embodiment of a dental flossing device 10 in use, with FIGS. 2 and 3 illustrating an actuator mechanism and components of the dental flossing device 10. The dental flossing device 10 has an elongate handle 12 having a main body 11, a handgrip end 14 and an opposite floss holder end 16, with an elongate flexible member, such as a flexible cable 18, installed in conjunction with the handle 12, such as within the handle 12, and extending through an axial passage 20 in the main body 11 to the floss holder end 16 thereof, as shown in FIG. 3 of the drawings.

The axial passage 20 is relatively narrow, having a diameter only slightly greater than that of the flexible member, such as that of the flexible cable 18. This can assist in preventing the flexible cable 18 from bending significantly when actuated and placed in a compression state, such as during flossing, the axial passage 20 guiding the flexible cable 18 along its intended path of travel. The dental flossing device 10 and components thereof can be made of various suitable materials, or combinations thereof, such as suitable plastic and metallic materials, as can depend on the use or application, and should not be construed in a limiting sense.

The flexible member, such as the flexible cable 18, has an actuator portion 22 disposed generally through the central portion of the handle 12, an actuator end 24 that connects to an actuator mechanism 29, a relatively short distal portion 26 opposite the actuator portion 22 and substantially orthogonal thereto, and a distal end 28 that connects removably to a floss holder 44 of the dental flossing device 10. The actuator mechanism 29 includes a slide 30 that is attached to the actuator end 24 of the flexible member, such as the flexible cable 18, with the slide 30 residing in a slide receptacle 32 in the handle 12, as shown in FIGS. 2 and 3 of the drawings.

Figure 5:
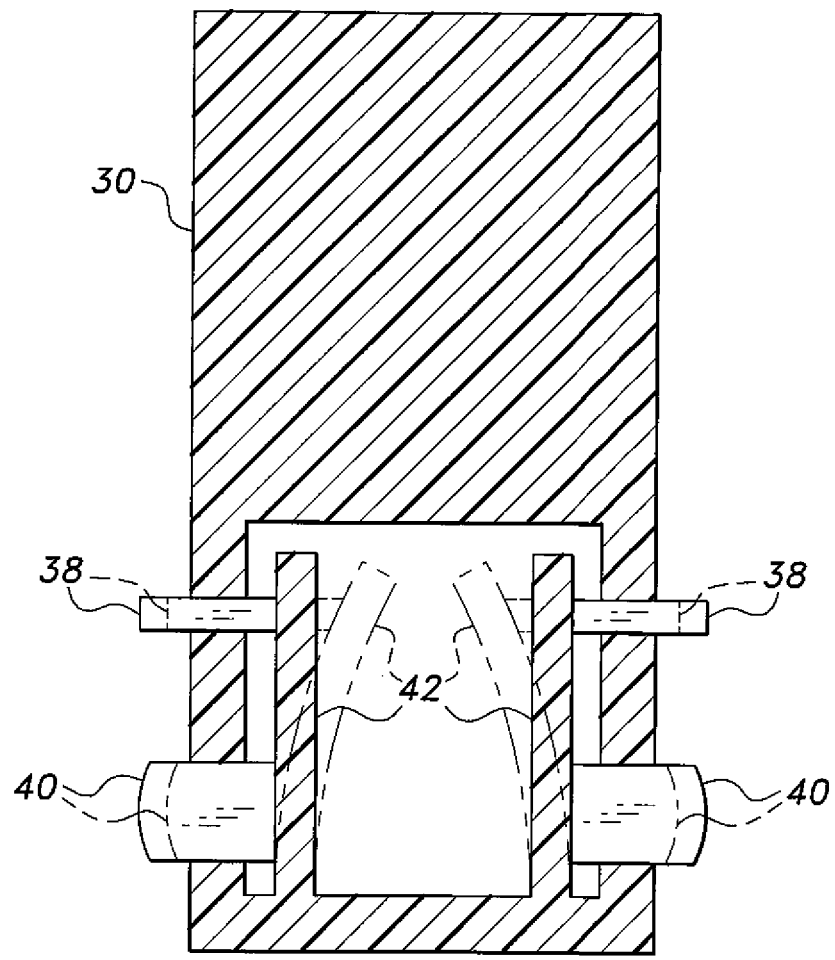
FIG. 5 is a detailed elevation view in section showing components of an internal mechanism of an embodiment of a slide component an embodiment of a dental flossing device according to the present invention.

The length or degree of travel of the slide 30, and corresponding travel of the flexible member, such as the flexible cable 18, can be selected by the user of the dental flossing device 10. The slide receptacle 32 has opposed, inwardly disposed first and second lateral shoulders, respectively 34*a* and 34*b*, therealong. Each pair of shoulders 34*a* and 34*b* are separated from one another and define corresponding laterally opposed slide pin receptacles 36 therebetween. The slide pin receptacles 36 and the first and second lateral shoulders 34*a* and 34*b* define slide limit stops to limit a range of movement or travel of the slide 30. The slide 30 includes opposed lateral pins 38 selectively extending therefrom, as shown in FIGS. 2 and 5 of the drawings. Retraction of the opposed lateral pins 38 is controlled by corresponding laterally opposed buttons 40 on opposing sides of the slide 30.

The buttons 40 are in communicating relation with two internal arms 42 positioned within the slide 30. Depressing the buttons 40 cause the two internal arms 42 to flex inward to retract the opposed lateral pins 38 that extend laterally from the distal ends of the internal arms 42, generally as shown in broken lines in FIG. 5 of the drawings. Releasing the buttons 40 allows the pins 38 to spring back to their extended positions, as shown in solid lines in FIG. 5. When the opposed lateral pins 38 are extended, they respectively contact the shoulders 34*a* and 34*b* to limit the travel of the slide 30 to only the distance between the shoulders 34*a* and 34*b*. Depressing the buttons 40 on the slide 30 retracts the pins 38, thereby allowing the slide 30 to travel the complete length of the slide receptacle 32.

Figure 4:
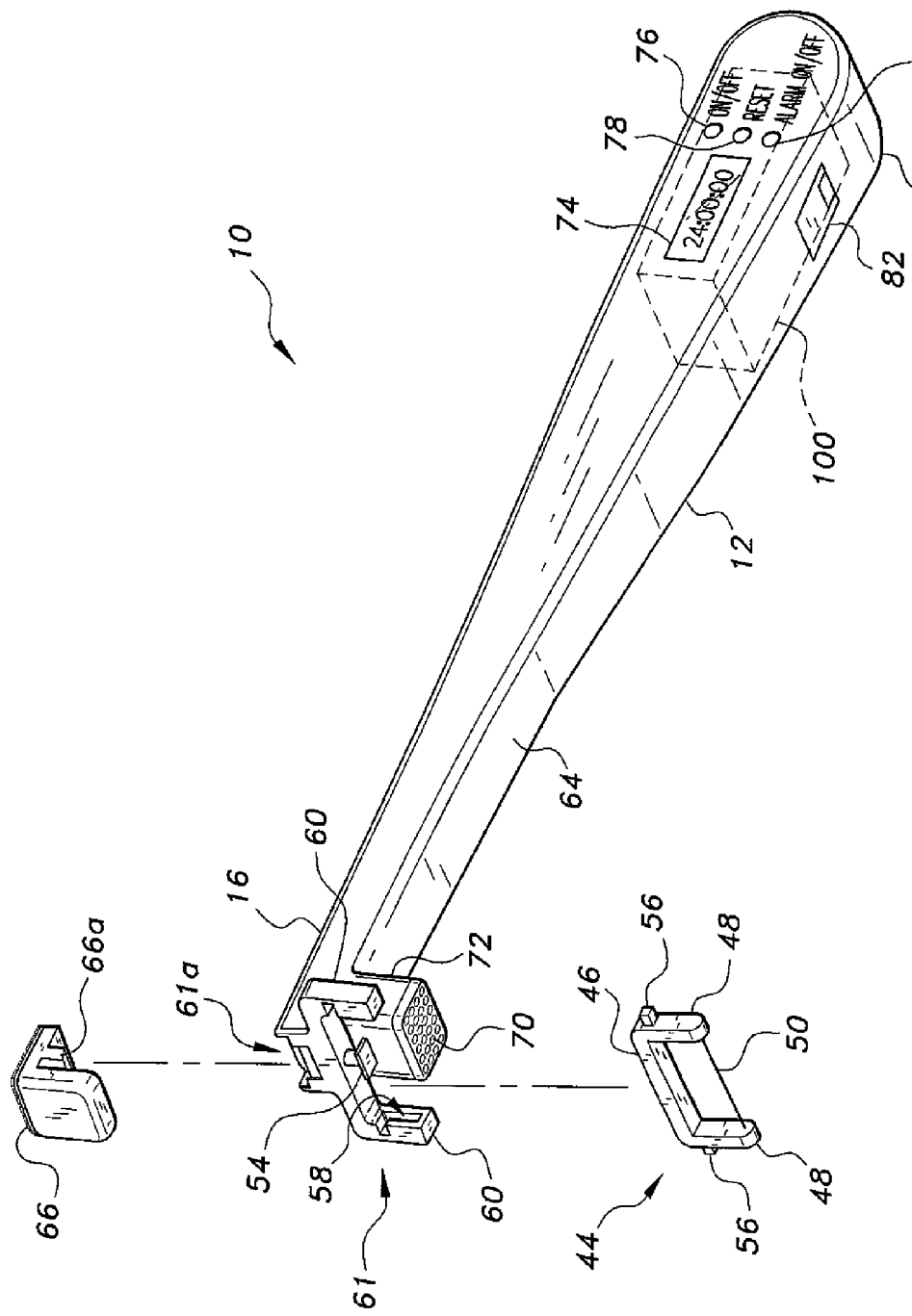
FIG. 4 is an exploded bottom perspective view of an embodiment of the dental flossing device of FIG. 1 according to the present invention, showing various removably attached components thereof.

The floss holder 44 is a relatively simple, desirably plastic, component that is economically manufactured and intended for disposal desirably after a single use, and the floss holder can be made of any of various suitable materials, such as various metallic or plastic materials, or combinations thereof, for example. FIGS. 2 and 4 provide clear illustrations of the floss holder 44. The floss holder 44 includes a lateral bar 46 with two laterally opposed arms 48 depending from the ends thereof. The floss holder 44 is adapted to have a short strand of dental floss 50 that is positioned in association with the floss holder 44, such as being positioned in extending relation between the arms 48. One or more of the floss holder 44 and the dental floss 50 is disposable after use, desirably after a single use of the floss holder 44 and the associated dental floss 50. The dental floss 50 desirably can be formed of any of various suitable materials for flossing, as is known in the art.

The lateral bar 46 has an upwardly oriented receptacle 52 in the center thereof, with the receptacle 52 removably engaging a catch 54 on the distal end 28 of the flexible member, such as the flexible cable 18. A floss holder retainer assembly 61 positioned at the distal end 16 of the handle 12 includes two laterally opposed floss holder guides 60 having corresponding channels 58. Two laterally opposed tabs 56 extend from the ends of the bar 46 and slide within corresponding channels 58 (see FIG. 4) formed within two laterally opposed floss holder guides 60 that depend from the distal end 16 of the handle 12.

When the receptacle 52 is in engaging relation with the catch 54 on the distal end 28 of the flexible member, such as the flexible cable 18, pushing the slide 30 in a forward direction toward the distal or floss holder end 16 of the handle 12 results in corresponding movement of the flexible member, such as the flexible cable 18, in the axial passage 20. The forward movement of the slide 30 toward the distal end 16 of the handle 12 enables the distal end portion 26 of the flexible member, such as the flexible cable 18, to move in a direction substantially orthogonal to the main body 11 of the handle 12, by the flexible cable 18 curving around in a downward direction in a portion of the axial passage 20 in the distal end portion 16 of the handle 12. Such forward movement of the slide 30 drives the floss holder 44 including the dental floss 50 from an initial position in a downward direction generally orthogonally relative to the length of the handle 12, i.e., in a direction away from the distal end 16 of the handle 12, generally as shown in FIG. 1 of the drawings, such as indicated by a double arrowed line 13.

Movement of the slide 30 in a reverse direction toward the handgrip end 14 of the handle 12 causes the floss holder 44 including the dental floss 50 to move in an upward direction generally orthogonally relative to the length of the handle 12 toward and to the initial position of the floss holder 44. The movement of the slide 30 in the reverse direction is accomplished by releasing the slide 30, with a compression spring 31 (shown in FIGS. 2 and 3) pushing the slide 30 in the reverse direction back toward the handgrip end 14 of the handle 12 to draw the floss holder 44 including the dental floss 50 back toward the distal end 16 of the handle 12 by a return movement of the flexible member, such as the flexible cable 18, that is in communication with the floss holder 44.

The reciprocal type action of selectively moving the floss holder 44 in a downward direction and in an upward direction relative to the distal end 16 of the handle 14 is illustrated by the double arrowed line 13 and can be repeated as desired, to perform a flossing action on one or more teeth of a user of the dental flossing device 10. The reciprocal movement of the slide 30 in the forward direction toward the distal end 16 of the handle 12 and in the reverse direction toward the handgrip end 14 of the handle 12 is illustrated by a double arrowed line 27.

When flossing is completed, the floss holder 44 can be unclipped from the catch 54 on the distal end 28 of the flexible member, such as the flexible cable 18, and the two tabs 56 slid from the channels 58 in the floss holder guides 60 depending from the distal end 16 of the handle 12 for convenient disposal, and a new floss holder 44 including the dental floss 50 can then be installed in the laterally opposed floss holder guides 60 that depend from the distal end 16 of the handle 12.

The distal end 16 of handle 12 of the dental flossing device 10 is desirably intended to be gripped between upper teeth UT and lower teeth LT during flossing, generally as shown in FIG. 1 of the drawings. When flossing one or more of the LT, the dental flossing device 10 is generally positioned as illustrated in FIG. 1 with the floss holder 44 including the dental floss 50 positioned in facing relation to the LT. Similarly, when flossing one or more of the UT, the dental flossing device 10 is generally positioned with the floss holder 44 including the dental floss 50 positioned in facing relation to the UT. Accordingly, a resilient upper bite pad 68 and a resilient lower bite pad 70 are respectively installed upon the corresponding upper and lower surfaces 62 and 64 at the distal end portion 16 of the handle 12.

The upper bite pad 68 typically can include two portions, a removable floss holder lock portion 66 and a fixed bite pad portion 67. The removable floss holder lock portion 66 of the upper bite pad 68 is positioned above and in overlying relation to the floss holder 44 when the removable floss holder lock portion 66 is installed on the distal end portion 16 of the handle 12. The removable floss holder lock portion 66 includes a locking tab 66a that, when the removable floss holder lock portion 66 is installed in overlying relation to the floss holder 44, the a locking tab 66a engages with a corresponding locking slot 61a on the floss holder retainer assembly 61 serving to lock or retain the floss holder 44 in its operable position. The engaging of the locking tab 66a with the corresponding locking slot 61a can assist in retaining the floss holder 44 in an operable position during use of the dental flossing device 10, such as when the upper and lower bite pads 68 and 70 are respectively positioned in engaging relation with one or more teeth of the UT and the LT during use, for example.

The fixed or permanently installed upper bite pad portion 67 is located immediately adjacent to the removable floss holder lock portion 66, but closer in relation to the handgrip end 14 of the handle 12. The fixed lower bite pad 70 is installed upon the lower surface 64 at the distal end 16 of the handle 12 or, more specifically, installed on an extension 72 depending from the lower surface 64 of the handle 12 in order to assist in providing relatively proper spacing for the floss holder 44 during actuation and use of the floss holder 44.

The act of flossing teeth must be relatively thoroughly done, if it is to be relatively effective in removing residual food deposits that can lead to bacterial buildup that can result dental problems. A very quick and/or superficial job of flossing the teeth does little good. Accordingly, the dental flossing device 10 includes timer and alarm systems as well, with the time being displayed on a display, such as on a display 74, disposed in the handgrip end 14 of the handle 12 and the timer and alarm systems being actuated by a series of control buttons 76, 78 and 80, for example, adjacent to the display 74 in conjunction with a control system, such as a generalized control system 100 of FIG. 6.

Figure 6:
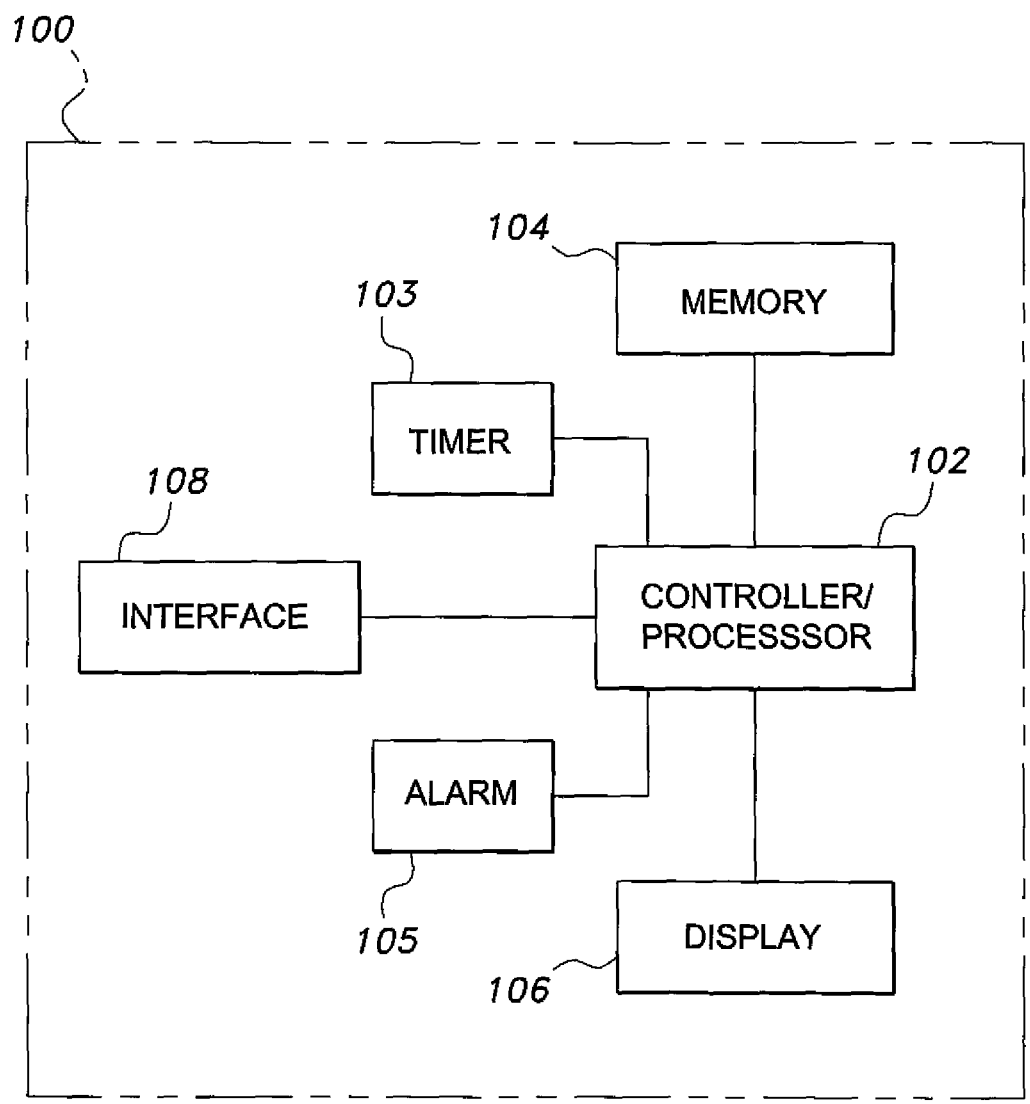
FIG. 6 is a block diagram of a generalized control system, including a controller/processor, a memory and an interface, as can be used for implementing a timer system and an alarm system in embodiments of a dental flossing device according to the present invention.

FIG. 6 illustrates the generalized control system 100 for implementing a timer system and an alarm system in the dental flossing device 10. The control system 100 includes a controller/processor 102, a memory 104, a display 106 and an interface 108, as well as including or being associated with a timer 103 for the timer system and an alarm 105 for the alarm system.

Data or control signals, such as to selectively activate or program the alarm 105 or to selectively set or program the timer 103 can be entered into the system 100 by a suitable type of interface 108, the interface 108 being in conjunction with the control buttons 76, 78 and 80 and the display 74, as a part of the display 106, to set, activate or deactivate the timer 103 and the alarm 105. Information and data related to the timer and alarm systems can be stored in computer readable memory 104, which can be any suitable type of computer readable and programmable memory, such as a semiconductor memory (for example, RAM, ROM, etc.).

Calculations and determinations for the timer and alarm systems are performed by the controller/processor 102, as can be incorporated on an integrated circuit (IC) chip, as can be any suitable type of computer processor, such as can include a programmable logic controller (PLC) or an application specific integrated circuit (ASIC), for example. The activation and deactivation of the alarm 103 and time count(s) from the timer 103 can be displayed to the user of the dental flossing device 10 on the display 74, which can be any suitable type of display such as a light emitting diode (LED) type display, for example.

The timer 103 can be any suitable type of timer and can be incorporated with the controller/processor 102. The alarm 105 can be any suitable type of alarm as can be incorporated with the controller/processor 102, the alarm providing a sound, a message, a light or vibration type alert, or a combination thereof, for example. The controller/processor 102, the timer 103, the memory 104, the alarm 105, the display 106 and the interface 108 are in communication with one another, such as by any suitable type of data bus, as is well known in the art.

The display 74 can display either an elapsed time between uses of the dental flossing device 10 or the duration of the flossing activity, depending upon the function selected by the control buttons, such as determined by pressing one or more of the control buttons 76, 78 and 80 or predetermined combinations thereof, for example. A timer control button 76 serves as an on/off switch for the timer 103, with the timer control button 76 acting as a toggle type switch or alternating between on and off functions or states for the timer 103, to selectively activate and deactivate the timer 103, with each press of the timer control button 76.

Turning the timer 103 on with the on/off timer control button 76 actuates a short timer, e.g., three to four minutes, such as a time period for a flossing operation to floss a substantial portion of the UT and the LT, although other time durations can be programmed, as desired. Pressing the on/off timer control button 76 can stop and can reset the timer 103 for a next use of the timer 103. The time information, such as time duration for a flossing operation, or a remaining time for a flossing operation, can be displayed on the display 74. The timer 103 can be reset to a predetermined time or an initial time at any time desired, such as by pressing the reset control button 78.

When the daily flossing operation has been completed the user can press an alarm control button 80, which selectively activates or deactivates the timer 103 to count a long timer, such as a 24 hour time period, or other suitable time period, as well as the alarm control button 80 can selectively deactivate the timer 103 and deactivate operation of the alarm 105. The alarm 105 can provide a visual alarm, such as on the display 74, or an audible alarm, such as a sound generated by a sound generator associated with the alarm 105, such as a speaker or buzzer. The alarm control button 80 similarly acts as a toggle type switch or alternating between on and off functions or states for the timer 103 and the alarm 105, to selectively activate and deactivate the timer 103 as a long timer and to selectively activate or deactivate operation of the alarm 105 including deactivating an alarm generated by the alarm 105, with each press of the alarm control button 80.

The timer 103 counts for 24 hours, or other suitable time period, and at the end of the 24 hour period, or other suitable time period, the timer 103 communicates with the controller/processor 102 to selectively activate the alarm 105, such as an audible alarm, e.g., conventional piezoelectric buzzer or other suitable device associated with the alarm 105 as can be contained within or adjacent to the handgrip portion 14 of the handle 12, as well as can flash alarm information, such as a visible alert or an alert message on the display 74, for example.

Actuating the on/off switch timer control button 76, before the 24 hour period has elapsed can reset the time between uses of the dental flossing device 10, such as resetting an elapsed time or a remaining time of a long timer to an initial time for a new long timer period, such as a new 24 hour period, or other suitable timer period, at that point, such new long timer period, when reset, commencing upon activation of the alarm control button 80, for example. The conventional electronics of the systems controlled by the various control buttons 76, 78 and 80 and the time or message alert displayed in the display 74 are powered by a small electrical storage cell or cells contained within the handle 12, such as one or more batteries, with access for removal and replacement being provided by a door or cover 82 (FIG. 4).

It is to be understood that the present invention is not limited to the embodiments described above, but encompasses any and all embodiments within the scope of the following claims.

I claim:

1. A dental flossing device, comprising:
an elongate handle having a handgrip end and a floss holder end opposite the handgrip end;
an elongate, flexible member reciprocatingly disposed in conjunction with the handle, the flexible member having an actuator portion, an actuator end, a distal portion opposite the actuator portion, and a distal end opposite the actuator end, the distal portion of the flexible member being generally orthogonal to the actuator portion of the flexible member; and
a floss holder removably disposed upon the floss holder end of the handle, the floss holder adapted to have a strand of dental floss positioned in association with the floss holder, the floss holder being removably attached to the distal end of the flexible member, selective forward and reverse movement of the flexible member selectively reciprocating movement of the floss holder and the dental floss relative to the floss holder end of the handle.

2. The dental flossing device according to claim 1, further comprising:
an upper bite pad disposed upon an upper surface of the handle at the floss holder end of the handle; and
a lower bite pad disposed upon a lower surface of the handle at the floss holder end of the handle.

3. The dental flossing device according to claim 2, wherein the upper bite pad comprises:
a fixed bite pad portion; and
a removable floss holder lock portion.

4. The dental flossing device according to claim 1, further comprising:
a display disposed upon the handle to display information including at least one of time information or alarm information; and
timer and alarm controls disposed upon the handle to selectively activate and deactivate a timer and an alarm positioned in conjunction with the handle.

5. The dental flossing device according to claim 1, wherein the floss holder and the dental floss associated with the floss holder are adapted for disposal after use.

6. The dental flossing device according to claim 1, further comprising:
a slide receptacle disposed on the handle; and
a slide disposed within the slide receptacle, the slide being attached to the actuator end of the flexible member.

7. The dental flossing device according to claim 6, wherein the slide receptacle has opposed pairs of first and second lateral shoulders,
a slide pin receptacle is respectively disposed between each corresponding pair of opposed first and second lateral shoulders of the slide receptacle, the first and second lateral shoulders and the slide pin receptacles defining slide limit stops, and
the slide has opposed lateral pins selectively retracting therein and extending therefrom, the opposed lateral pins when selectively engaging the respective slide pin receptacles correspondingly limit a range of travel of the slide in the slide receptacle.

8. A dental flossing device, comprising:
an elongate handle having a handgrip end, a floss holder end opposite the handgrip end, an upper surface, and a lower surface opposite the upper surface;
a slide receptacle disposed on the handle;
a slide disposed within the slide receptacle;
a floss holder removably disposed upon the floss holder end of the handle, the floss holder extending generally orthogonally from the lower surface of the floss holder end of the handle, the floss holder adapted to have a strand of dental floss positioned in association with the floss holder, the floss holder adapted for reciprocating movement relative to the floss holder end of the handle;
an upper bite pad disposed upon the upper surface of the handle at the floss holder end of the handle;
wherein the upper bite pad includes a fixed portion and a removable floss holder lock portion; and
a lower bite pad disposed upon the lower surface of the handle at the floss holder end of the handle.

9. The dental flossing device according to claim 8, further comprising:
an elongate, flexible cable reciprocatingly disposed in conjunction with the handle, the flexible cable having an actuator portion, an actuator end, a distal portion opposite the actuator portion, and a distal end opposite the actuator end, the distal portion of the flexible cable being generally orthogonal to the actuator portion of the flexible cable, the floss holder being removably attached to the distal end of the flexible cable, selective movement of the flexible cable selectively reciprocating movement of the floss holder and dental floss relative to the floss holder end of the handle.

10. The dental flossing device according to claim 8, further comprising:
a display disposed upon the handle to display information including at least one of time information or alarm information; and
timer and alarm controls disposed upon the handle to selectively activate and deactivate a timer and an alarm positioned in conjunction with the handle,
wherein the alarm generates at least one of a visual alarm or an audible alarm.

11. The dental flossing device according to claim 8, wherein the floss holder and the dental floss associated with the floss holder are adapted for disposal after a single use.

12. The dental flossing device according to claim 8,
wherein the slide being attached to a flexible cable, the flexible cable being in communication with the floss holder, selective movement of the flexible cable by the slide selectively reciprocating movement of the floss holder relative to the floss holder end of the handle.

13. The dental flossing device according to claim 12, wherein
the slide receptacle has opposed pairs of first and second lateral shoulders,
a slide pin receptacle is respectively disposed between each corresponding pair of opposed first and second lateral shoulders of the slide receptacle, the first and second lateral shoulders and the slide pin receptacles defining slide limit stops, and
the slide has opposed lateral pins selectively retracting therein and extending therefrom, the opposed lateral pins when selectively engaging the respective slide pin receptacles correspondingly limit a range of travel of the slide in the slide receptacle.

14. A dental flossing device, comprising:
an elongate handle having a handgrip end, a floss holder end opposite the handgrip end, an upper surface, and a lower surface opposite the upper surface;
an elongate, flexible member being reciprocatingly disposed in association with the handle, and the elongate, flexible member having an actuator portion, an actuator end, a distal portion opposite the actuator portion, and a distal end opposite the actuator end, the distal portion of the flexible member being generally orthogonal to the actuator portion of the flexible member;
a floss holder extending generally orthogonally from the lower surface of the floss holder end of the handle, the floss holder adapted to have a strand of dental floss positioned in association with the floss holder, the floss holder adapted for selective reciprocating movement of the floss holder and the dental floss relative to the floss holder end of the handle;
wherein the floss holder being adapted to be removably attached to the flexible member;
a display disposed upon the handle to display information including at least one of time information or alert information; and
timer and alarm controls disposed upon the handle to selectively activate and deactivate a timer and an alarm positioned in conjunction with the handle.

15. The dental flossing device according to claim 14,
wherein the floss holder further adapted to be removably attached to the distal end of the flexible member, and the flexible member selectively reciprocating movement of the floss holder and the dental floss relative to the floss holder end of the handle.

16. The dental flossing device according to claim 14, further comprising:
a first upper bite pad portion fixedly disposed upon the upper surface of the handle at the floss holder end of the handle;
a second upper bite pad portion removably disposed upon the upper surface of the handle at the floss holder end of the handle, the second upper bite pad portion including a floss holder lock portion adapted to engage with a floss holder retainer assembly positioned at the floss holder end of the handle to retain the floss holder in an operable position; and
a lower bite pad disposed upon the lower surface of the handle at the floss holder end of the handle.

17. The dental flossing device according to claim 14, wherein the floss holder and the dental floss are adapted for disposal after a single use.

18. The dental flossing device according to claim 14, further comprising:
a slide receptacle disposed on the handle; and
a slide disposed within the slide receptacle, the slide being attached to the flexible member, the flexible member being in communication with the floss holder, selective movement of the flexible member by the slide selectively reciprocating movement of the floss holder relative to the floss holder end of the handle.

19. The dental flossing device according to claim 18, wherein
the slide receptacle has opposed pairs of first and second lateral shoulders,
a slide pin receptacle is respectively disposed between each corresponding pair of opposed first and second lateral shoulders of the slide receptacle, the first and second lateral shoulders and the slide pin receptacles defining slide limit stops, and
the slide has opposed lateral pins selectively retracting therein and extending therefrom, the opposed lateral pins when selectively engaging the respective slide pin receptacles correspondingly limit a range of travel of the slide in the slide receptacle.

\* \* \* \* \*